United States Patent [19]

Sekiguchi et al.

[11] Patent Number: 5,109,127
[45] Date of Patent: Apr. 28, 1992

[54] NONIONIC SURFACE ACTIVE AGENT

[75] Inventors: Shizuo Sekiguchi; tomoko Yasumasu, both of Funabashi; Hiroshi Miyake, Narashino; Yoshihisa Endo, Sakura, all of Japan

[73] Assignee: Lion Corporation, Tokyo, Japan

[21] Appl. No.: 608,738

[22] Filed: Nov. 5, 1990

[30] Foreign Application Priority Data

Nov. 6, 1989 [JP] Japan ................... 1-288154

[51] Int. Cl.$^5$ ................... A61K 7/16; C11D 1/66
[52] U.S. Cl. ................... 536/115; 536/127; 536/119; 536/18.3; 536/4.1; 51/25; 51/23; 252/547; 252/174.17
[58] Field of Search ............ 514/25, 23; 536/115, 536/119

[56] References Cited

U.S. PATENT DOCUMENTS

| | | | |
|---|---|---|---|
| 557,925 | 5/1858 | Barsky | 536/115 |
| 2,973,353 | 2/1961 | Gaertner | 536/119 |
| 3,231,561 | 1/1966 | Burnelle et al. | 536/115 |
| 4,713,447 | 12/1987 | Letton | 536/18.6 |
| 4,748,158 | 5/1988 | Biermann et al. | 514/25 |
| 4,778,881 | 10/1988 | Nieuwenhuis et al. | 536/115 |
| 4,806,275 | 2/1989 | Johnson et al. | 536/115 |
| 4,973,489 | 11/1990 | Meyer et al. | 536/115 |

FOREIGN PATENT DOCUMENTS

WO88/10147 12/1988 PCT Int'l Appl. .
WO89/01480 2/1989 PCT Int'l Appl. .
WO90/08182 7/1990 PCT Int'l Appl. .
WO90/09451 8/1990 PCT Int'l Appl. .

*Primary Examiner*—Ronald W. Griffin
*Assistant Examiner*—Louise Leary
*Attorney, Agent, or Firm*—Birch, Stewart, Kolasch & Birch

[57] ABSTRACT

A nonionic surface active agent comprising a fatty acid ester of a hexose sugar or an alkyl glycoside thereof, wherein the content of monoester is from 93 to 99.9% by weight, the content of diester is from 0.1 to 7% by weight and the content of tri- and higher polyesters is from 0 to 1% by weight in the fatty acid ester.

7 Claims, No Drawings

NONIONIC SURFACE ACTIVE AGENT

BACKGROUND OF THE INVENTION

1. Field of the Invention

The present invention concerns a nonionic surface active agent comprising a fatty acid ester of a hexose having a ketone or aldehyde group, such as glucose, galactose and fructose, or an alkyl glycoside of such hexose. More particularly, it relates to a nonionic surface active agent which is substantially tasteless and displays excellent foaming power.

2. Description of the Prior Art

Although various surface active agents have heretofore been used as foaming agents, the kinds of surface active agents usable in oral or tasted commercial products, such as dentifrices and foods, are restricted because of safety concerns regarding toxicity, stimulation and exfoliation of oral mucous membrane. For instance, sodium lauryl sulfate, sucrose fatty acid ester, polyglycerol fatty acid ester and acylated amino acid derivatives have been mainly used as the foaming agent for dentifrices, while sucrose fatty acid ester, polyglycerol fatty acid ester and sorbitol fatty acid ester have been mainly used in foods.

However, since all of these surface active agents exhibit bitterness or an oily taste when held in the mouth, special seasoning is required when using them. In addition, since the taste of the surface active agents per se is not favorable, the amounts thereof have to be restricted. Moreover, all of the surface active agents described above except for sodium lauryl sulfate show poor foaming power when used as the foaming agent in dentifrice.

SUMMARY OF THE INVENTION

An object of the present invention is to provide a substantially tasteless nonionic surface active agent giving neither bitterness nor oily taste, and having a satisfactory foaming power with high safety.

The present inventors have made an earnest study for satisfying the foregoing demands and, as a result, have found that a substantially tasteless nonionic surface active agent having excellent foaming power can be obtained by controlling the content of monoester as from 93 to 99.9% by weight, the content of diester as from 0.1 to 7% by weight and the content of triester and higher polyesters as from 0 to 1% by weight in a fatty acid ester of a hexose having a ketone or aldehyde group such as glucose, galactose, fructose, etc. or the alkyl glycoside of such hexose.

Specifically, fatty acid esters of hexose have heretofore been known (for example, refer to U.S. Pat. Nos. 2,973,353 and 3,231,561, and International Patent Laid-Open WO. 88/10147). However, in the process for synthesizing fatty acid esters of hexose, typically glucose, known in the prior art, including the production process as described in the above-mentioned, a great amount of triester or higher polyester is contained in the resultant ester composition and the monoester content is only about 40 to 50% by weight.

For instance, fatty acid esters obtained by the process of International Patent Laid-Open WO 88/10147, usually contain monoester of from 40 to 50% by weight, diester of from 40 to 45% by weight and triester or higher polyester of about 5 to 20% by weight. Then, in the above-mentioned known literatures, mono-, di-, tri- or higher polyesters are used as they are as an ester mixture. Further, the monoester is a mixture of a glucose mono-esterified at the 3-position and a glucose mono-esterified at the 6-position.

However, according to the study of the present inventors, such mixed fatty acid esters of hexose have bitterness or oily taste which are as keen as those of other nonionic surface active agents and, show only the same extent of foaming power as compared with those of other nonionic surface active agents in the prior art. Accordingly, they lack in the merit capable of driving out other nonionic surface active agents such as sucrose fatty acid monoester or diester, sorbitan fatty acid monoester or diester, or polyglycerol fatty acid monoester or diester, although such nonionic surface active agent has bitterness or oily taste and, thus, bad taste.

Surprisingly, it has been found that the fatty acid ester of hexose or the alkyl glycoside thereof having the content of the monoester as from 93 to 99.9% by weight, the content of the diester as from 0.1 to 7% by weight and the content of the triester and higher polyesters as from 0 to 1% by weight and, in particular, 0 to 0.5% by weight is substantially tasteless and has a satisfactory foaming power. The present invention has been accomplished based on such a finding.

Accordingly, there is provided by the present invention a nonionic surface active agent comprising a fatty acid ester of hexose or an alkyl glycoside thereof, wherein the content of monoester is from 93 to 99.9% by weight, the content of diester is from 0.1 to 7% by weight and the content of the triester and higher polyesters is from 0 to 1% by weight in the fatty acid ester.

DETAILED DESCRIPTION OF THE INVENTION

The nonionic surface active agent according to the present invention comprises fatty acid ester of a hexose or an alkyl glycoside thereof, which can be obtained from a hexose or an alkyl glycoside thereof and a fatty acid or a derivative thereof such as a fatty acid lower alkyl ester.

As the hexose, monohexose, for example, glucose, galactose or fructose is suitable, glucose being particularly preferred.

The glucose can been prepared by acidic or enzymatic hydrolysis of starch such as corn or potato and subsequent decoloration and purification. There can be mentioned, for example, crystalline glucose, powdery glucose or granular glucose as defined in JAS.

As the alkyl glycoside of the hexose, alkyl glycoside with an alkyl group having 1 to 6 carbon atoms is preferred. This is prepared by adding a fatty acid alcohol with 1 to 6 carbon atoms to a hexose. Examples thereof include, 1-methyl glucoside, 1-ethyl glucoside, 1-butyl glucoside or 1-amyl glucoside, and those commercially available from Stailley Co. can be used.

As the fatty acid, those having 6 to 20, particularly, 6 to 12 carbon atom, are preferred. Various fatty acids including natural or synthetic products, saturated or unsaturated acids, and linear or branched structures can be used alone or as a mixture. The acid may have one or two hydroxy groups. Specifically, there can be mentioned as natural fatty acids, for example, saturated or unsaturated linear fatty acids such as caproic acid, enanthic acid, caprylic acid, pelargonic acid, decanoic acid, lauric acid, myristic acid, palmitic acid, stearic acid, linolic acid, oleic acid, capric acid and undecanoic acid obtained by hydrolyzing vegetable oils and animal oils such as coconuts oil, palm oil, tallow, linseed oil and soybean oil. As synthetic fatty acids, there may be used a mixture of linear or branched fatty acids prepared by oxidizing olefin polymers. It is also possible to use fatty acids derived from microorganisms such as γ-linolenic acid. Further, as the lower alkyl ester of the fatty acid, alkyl esters having 1 to 8 carbon atoms such as methyl, ethyl or propyl ester of the fatty acid described above can be used. Halogenated products of the fatty acid can also be used as the starting material.

The fatty acid esters of hexose or the alkyl glycoside thereof can be synthesized by using various known methods, including ester synthesis using lipase and the like. For example, (1) an ester exchange reaction between starting oils or fats and a hexose or its alkyl glycoside, (2) an ester exchange reaction between a lower alkyl ester of a fatty acid and a hexose or its alkyl glycoside, or (3) an ester synthesis between a fatty acid and a hexose or its alkyl glycoside. In addition, a synthesis process using a fatty acid chloride and a hexose or its alkyl glycoside may also be employed.

However, since esters produced by any of these known processes contain less monoester and more triester or higher polyester, it is necessary to laboriously fractionate and isolate after synthesis in order to obtain an ester of high monoester content. Accordingly, a method of using a thermostable lipase proposed in U.S. patent application Ser. No. 07/566,220 or European Patent Application No. 90115575.4 is preferably adopted for the production of the monoester.

The surface active agent (a fatty acid ester of a hexose or alkyl glycoside thereof) according to the present invention contains from 0 to 1% by weight, particularly, 0 to 0.5% by weight of triester and higher polyesters, from 0.1 to 7% by weight, particularly, 0.2 to 4% by weight of diester and from 93 to 99.9% by weight, particularly, 96 to 99.8% by weight of monoester. In the monoester, OH groups may be esterified at any one of the 1,2,3,4 and 6-positions of glucose, in the case of a glucose ester, and at any one of 2,3,4 and 6-positions of glucose in the case of a glucoside ester. Particularly, those in which the OH group at the 6-position is esterified, represented by the following formula (I), are preferred:

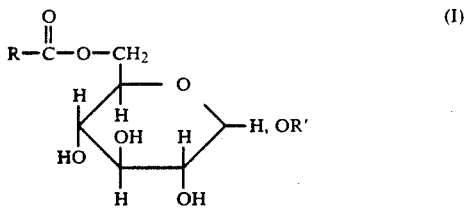

where R represents a fatty acid residue with 6 to 20, particularly, 6 to 12 carbon atoms and R' represents a hydrogen atom or an alkyl group having 1 to 6 carbon atoms.

Examples of such glucose fatty acid esters include glucose-6-caprylmonoester, glucose-6-decanoate monoester, glucose-6-laurylmonoester, glucose-6-myristylmonoester, glucose-6-palmitylmonoester, glucose-6-oleylmonoester and glucose-6-γ-linolate monoester.

Further, as the alkyl glycoside fatty acid ester with 1 to 6 carbon atoms, there can be mentioned, for example, 1-methyl-6-caprylglucoside, 1-ethyl-6-caprylglucoside, 1-ethyl-6-laurylglucoside, 1-butyl-6-caprylglucoside, 1-ethyl-6-palmitylglucoside and 1-ethyl-6-oleylglucoside.

The surface active agent according to the present invention can be used for various applications, for which the conventional nonionic surface active agents have been used and it is, particularly, effective for such uses as requiring for taste, for example, oral compositions such as dentifrices or foods. In addition, it can also be used suitably to shampooes and like other detergents.

The surface active agent according to the present invention can be used singly or in combination.

In this case, a nonionic surface active agent having excellent foaming power, satisfactory foam feeling and mildness to hands and skin can be prepared by using a monooctanoate of glucose or glucoside and a monodecanoate of glucose or glucoside at a weight ratio of from 95:5 to 10:90, more preferably, 95:5 to 30:70.

Accordingly, the combined system can be used effectively for oral compositions such as dentifrice, detergents such as dish-wash detergent and skin-care or hair-care products such as shampoo, body shampoo and face cleansing agent.

The surface active agent according to the present invention can further be used in combination with other surface active agents.

When the surface active agent according to the present invention is used in an oral composition, such as dentifrice, the foaming power and feeling upon use can be further improved by combining one or more of the water-soluble salts of alkyl sulfates, N-acylamino acids or N-acylmethyl taurines.

As the salts of alkyl sulfates, those sulfate esters of saturated or unsaturated alcohols having 8 to 18 carbon atoms, preferably 12 to 14 carbon atoms are preferred. Specifically, sodium lauryl sulfate, sodium myristyl sulfate, or the like is preferably used.

As the salts of N-acylamino acids, there can be used suitably N-long chained acylamino acid salts, particularly, those having saturated or unsaturated acyl groups having 8 to 18 carbon atoms, specifically, lauroyl group, myristoyl group, palmitoyl group, stearoyl group, oleoyl group, coconut oil fatty acid residue, hardened tallow fatty acid residue or mixed residues of such fatty acids. There is no particular restrictions for the kind of the amino acid and it is preferred to use glutamic acid, sarcosine or N-methyl-β-alanine singly or in combination. Examples of the N-acylamino acid salts include sodium salts, potassium salts, etc. of N-lauroyl glutamate, N-myristoyl glutamate, N-lauroyl sarcosinate, N-myristoyl sarcosinate and N-lauroyl-N-methyl-β-alaninate. The blending amount of the N-acyl amino acid salt is preferably 0.5% by weight or less in case of using for an oral composition. If it is used in excess of 0.5% by weight, exfoliation of oral mucous membrane may be caused.

The N-acylmethyl taurine salt has 8 to 16 carbon atoms, more preferably, 12 to 14 carbon atoms in the acyl group. If the number of carbon atoms in the acyl group is less than 8, taste is poor. On the other hand, if it is more than 16, the foaming property is undesirably reduced. In this case, the acyl group may be saturated or unsaturated, although a saturated acyl group is preferred. The N-acylmethyl taurine salt has the following formula (I):

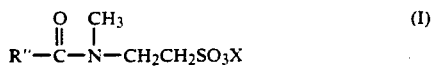

where R" represents a residue of a saturated or unsaturated fatty acid having 8 to 16 carbon atoms and X represents an alkali metal, alkaline earth metal, ammonium or organic amine. Specifically, there can be mentioned, for example, sodium N-caproylmethyl taurine, sodium N-lauroylmethyl taurine, sodium N-myristoylmethyl taurine, sodium N-palmitoylmethyl taurine and sodium N-coconut oil fatty acid methyl taurine. They may be used alone or in combination.

In case of using surface active agent according to the present invention for an oral composition in combination with water-soluble salts of alkyl sulfates, N-acylamino acids and N-acylmethyl taurines, it is preferred to use a glucose or glucoside fatty acid ester having 8 to 14 carbon atoms in the acyl group as the surface active agent according to the present invention in view of the taste and the foaming property. The blending ratio is from 1 to 10% by weight, particularly, 0.5 to 5% by weight based on the entire composition.

The alkyl sulfate salt and the glucose and/or glucoside fatty acid ester is preferably used at a weight ratio of from 1:4 to 4:1, particularly 1:3 to 2:1. If the ratio of the glucose and/or glucoside fatty acid ester is increased in excess of ¼, the foaming power may sometime be deteriorated. On the other hand, if the ratio of the alkyl sulfate salt is increased in excess of 4/1, there may be recognized no sufficient effect for reducing stimulation to oral mucous membrane. In this case, the total blending amount of the alkyl sulfate salt and the glucose and/or glucoside fatty acid ester is preferably from 0.01 to 10% by weight and, more preferably, from 0.1 to 5% by weight.

The N-acylmethyl taurine salt and the glucose and/or glucoside fatty acid ester is preferably used together at a weight ratio of from 1:4 to 4:1, particularly, 1:3 to 1:1. If the ratio of the glucose and/or glucoside fatty acid ester is increased in excess of ¼, synergistic effect for the foaming property may not be obtained sufficiently. On the other hand, if the ratio of the N-acylmethyl taurine salt is increased in excess of 4/1, deposition of N-acylmethyl taurine salt is remarkably increased in a low temperature storage and the stability of the composition may be deteriorated. The total blending ratio of N-acylmethyl taurine salt and glucose and/or glucoside fatty acid ester is preferably from 0.1 to 5% by weight, more preferably, from 0.5 to 2% by weight.

When the surface active agent according to the present invention is used for a shampoo composition, feeling upon rinsing and storage stability can be improved by the combined use with an amphoteric surface active agent and slimy feeling can be improved by the combined use of an anionic surface active agent.

In this case, any amphoteric surface active agents usually employed for shampoo compositions including imidazoline type amphoteric surface active agent, alkyl betaine type amphoteric surface active agent, sulfo betaine type amphoteric surface active agent, aminocarboxylic acid salt type amphoteric surface active agent and amide betaine type amphoteric surface active agent can be used.

When the surface active agent according to the present invention is blended in combination with the amphoteric surface active agent for a shampoo composition, a fatty acid ester having 6 to 20, particularly, 6 to 12 carbon atoms, in the acyl group of glucose or alkyl glucoside having 1 to 4 carbon atoms in the alkyl group is preferred and the blending amount is from 0.1 to 30% by weight, particularly, from 1 to 20% by weight based on the entire composition. Further, the blending amount of the amphoteric surface active agent is from 0.1 to 30% by weight, particularly, 1 to 15% by weight based on the entire composition.

As the anionic surface active agent, any of those employed usually for the shampoo compositions may be used. There can be mentioned, for example, fatty acid type surface active agent such as fatty acid salt (soap), glycerol monoalkyl ester monosulfate salt, coconut oil fatty acid-collagen condensate and protein-fatty acid condensate, higher alcohol type surface active agent such as alkyl sulfate salt, polyoxyethylene alkyl ether sulfate salt and monoalkyl sulfosuccinate salt, as well as α-olefine sulfonate, acyl sarcosinate salt, acyl glutamate salt, paraffin sulfonate, succinic acid monoglyceride, monoglycerol sulfate, polyoxyethylene coconut oil fatty acid amide ether sulfate, N-acylmethyl taurine salt and N-acyl-N-methyl-β-alaninate.

When the surface active agent according to the present invention is blended together with the anionic surface active agent in a shampoo composition, a glucose fatty acid ester having 11 to 20, particularly, 11 to 18 carbon atoms in the acyl group and an alkyl glucoside fatty acid ester having 11 to 20, particularly 11 to 18 carbon atoms in the acyl group and 1 to 4 carbon atoms in the alkyl group is preferred as the surface active agent according to the present invention, and the blending ratio thereof is from 0.1 to 30% by weight, particularly, 1 to 20% by weight based on the entire composition. Further, the blending amount of the anionic surface active agent is from 0.5 to 30% by weight, particularly, 1 to 20% by weight based on the entire composition.

When the surface active agent according to the present invention is blended to a detergent such as a dishwash detergent and a house-hold detergent, slimy feeling upon cleaning can be prevented and rinsing property can be improved by the combined use with one or more of the following surface active agents (i)-(vii):

(i): Higher alcohol sulfate salt (alkyl sulfate salt)

The number of carbon atoms in the alcohol chain is preferably from 8 to 20. The alcohol moiety may be linear or branched and may be saturated or unsaturated.

(ii): Amino acid surface active agent

Typical examples are acylated alaninate salt, acylated sarcosinate salt, acylated tauride salt, acylated glutamate salts, aminoacetic acid betaine and sulfobetaine.

(iii): $C_{10-18}$ α-olefine sulfonate (iv): Succinate salt

Salt of monoester of succinic acid and alcohol represented by the following general formula:

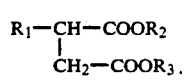

where $R_1$: hydrogen, alkyl or alkenyl group preferably having 8 to 16 carbon atoms, $R_2$, $R_3$: One is alkyl group preferably having 8 to 16 carbon atoms and another is hydrogen, alkali metal or alkaline earth metal, or both of them are hydrogen, alkali metal, alkaline earty metal or alkanol amine.

(v): Polyoxyethylene alkyl ether

An adduct of 2 to 15 mol in average ($\bar{p}=2-15$), preferably, 7 to 15 mol of ethylene oxide to primary or secondary alcohol with a straight chain rate of 50% by weight or more, preferably, 70% by weight or more. The alcohol may be saturated or unsaturated.

As the salt of the surface active agents, alkali metal, magnesium or mono-, di- or tri-ethanolamine salt may be used. Further, the blending amount of the surface active agents (i)-(v) described above in the detergent composition is from 0.5 to 20% by weight, particularly, 5 to 15% by weight.

(vi): alkylamine oxide

This is a surface active agent with less skin stimulation and mild to skin, represented by the following general formula. In the formula, $R_4$ and $R_5$ each represents an alkyl group or hydroxy alkyl group with 1 to 5 carbon atoms and $R_6$ represents an alkyl group with 8 to 20 carbon atoms.

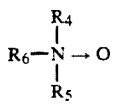

in which $R_6$ may be saturated or unsaturated and it may be linear or branched.

The alkylamine oxide is blended in an amount of from 0.5 to 10% by weight, preferably, 2.5 to 5.5% by weight in the detergent composition.

(vii): Fatty acid alkanolamide

This is a nonionic surface active agent with less skin stimulation and mild to skins. This is an amide of a fatty acid and an ethanol amine and a typical example is a fatty acid ethanolamide. As the fatty acid alkanolamide, those comprising 70% by weight or more, preferably, 85% by weight or more of $C_{12}$ fatty acid alkanolamide with 12 carbon atoms in the fatty acid residue are preferably used. As the content of the alkanolamide other than $C_{12}$ fatty acid alkanolamide is increased, occurrence of slimy feeling can not sufficiently be prevented.

The fatty acid alkanolamide is blended in the detergent composition in an amount of from 1 to 20% by weight, preferably, 4 to 10% by weight.

The surface active agent can be blended in an amount of from 3 to 40% by weight based on the entire composition. When the surface active agent according to the present invention is blended in combination with the surface active agents (i)-(vii) in the detergent composition, the blending amount of the surface active agent of the present invention is preferably from 1 to 30% by weight, particularly, 5 to 20% by weight based on the entire composition. In this case, the surface active agent having 6 to 18 carbon atoms in the acyl group is preferred as the surface active agent according to the present invention.

Further, when the surface active agent according to the present invention is blended in combination with a polyethylene glycol having a polymerization degree of ethylene oxide of 3 to 226, with the liquid detergent composition, film formation can be prevented. A liquid detergent is usually charged in a bottle type vessel and used by being discharged from a distribution cap. However, if film formation should occur, the distribution cap is clogged making the use difficult or the distribution hole is completely clogged. Use of the polyethylene glycol can prevent such a disadvantage.

In this case, the blending amount of the polyethylene glycol is from 0.5 to 5% by weight and, in particular, 1 to 3% by weight, while the blending amount of the surface active agent according to the present invention is from 1 to 30% by weight, particularly, 5 to 25% by weight based on the entire composition. The surface active agent according to the present invention preferably has 6 to 18 carbon atoms in the acyl group.

In case of preparing an oral composition or liquid detergent, known ingredients can be blended as additional ingredients.

For instance, an oral composition may be prepared and applied as toothpaste, toothpowder, liquid dentifrice, mouthwash and artificial teeth detergent. For the dentifrice, there can be used abrasives such as calcium secondary phosphate, calcium carbonate, calcium pyrophosphate, insoluble sodium metaphosphate, aluminum hydroxide, silica and silicate (blending amount: 10 to 95% by weight based on the entire composition), humectants such as glycerol, sorbitol, propylene glycol and polyethylene glycol (blending amount: 10 to 70% by weight based on the entire composition), binders such as sodium carboxymethyl cellulose, carrageenan, sodium alginate, Veegum ®, hydroxyethyl cellulose, xanthane gum and sodium polyacrylate (blending amount: 0.1 to 5% by weight based on the entire composition), sweetener such as sodium saccharine, glycyrrhizin, stevioside, paramethoxycinnamic aldehyde, neohesperidyl dihydrochalcone and perillartine, and flavors such as menthol, carvone and anethol. If required, fluorides such as sodium monofluorophosphate, sodium fluoride and tin fluoride, anti-inflammatory agents such as tranexamic acid, ε-aminocaproic acid and allantoinate, phosphoric acid compound such as sodium polyphosphate and like other phermaceutical agents can be used.

Further, customary ingredients may be blended also in other oral compositions and such oral compositions can be prepared by the conventional method.

The blending amount of the surface active agent according to the present invention in the oral composition is from 0.1 to 10% by weight based on the entire composition.

In a detergent such as a shampoo composition, ordinary ingredients may be added, as required, in addition to the surface active agent as described above, for example, foam improver such as alkanolamine or amine oxide, emulsifying agent such as higher fatty acid glycol ester or high molecular emulsion, hydrotrope such as ethanol, propylene glycol, polyethylene glycol or glycerol, emollient such as oil and fat, higher alcohol ester, lanolin derivative, protein derivative, squalane or cationized cellulose, viscosity improver such as cellulose derivative, polyvinyl alcohol, carboxyvinyl polymer, polyvinyl pyrrolidone and sodium chloride, preservative such as benzoic acid, benzoic acid ester or sorbic acid, metal chelating agent such as EDTA, NTA or citric acid, pH controller such as sodium phosphate, as well as UV-absorber, dandruff remover, pigment and perfume. A shampoo composition can be prepared into an appropriate form such as cream or liquid by a usual method.

The surface active agent according to the present invention can also be applied to a detergent such as cloth detergent, body shampoo, kitchen detergent and living detergent, for example, used for bath and toilet.

The blending amount of the surface active agent according to the present invention in the detergent is from 0.1 to 30% by weight, particularly, 1 to 20% by weight based on the entire amount.

Since the surface active agents according to the present invention hardly denature protein, effective ingredients composed of protein such as enzymes including dextranase and mutanase, and antisera antibodies against Strestpococcus mutans, Bacteroides gingivalis and Actinomyces viscosus and enzymes including glucose-transfarase are blended in a stable manner in a composition containing the surface active agent according to the present invention.

Next, Synthesis Examples for the surface active agent according to the present invention will be described below.

SYNTHESIS EXAMPLE 25 ml of tertiary butanol was added to a mixture of 5.00 g (27.64 mM) of glucose and 1.03 g (5.55 mM) of methyl caprinate, and 100 mg of thermostable lipase derived from Candida antarctica (sp-382, manufactued by NOVO Co.) immobilized into an acrylic resin was further added. Then, they were refluxed under heating while stirring for 24 hours with an addition of 10 g of molecular sieves 5A as a methanol remover, to obtain glucose monocaprinate ($C_{10}$ glucose ester).

Then, 0.5 ml of the reaction solution was taken into a screw tube, to which were added 2.5 ml of pyridine and, further, 10 μl of n-tetradecane as an internal standard substance and then mixed sufficiently. Then, they were filtered and 1 ml of acetic anhydride was added as an acetylating agent to 1 ml of the filtrate and reacted at 60° C. for 30 min.

When 1 μl of the reaction solution was analyzed on gas chromatography, glucose monocaprinate was obtained at a purity of 98% and a yield of 70%, in which the content of tri- or higher ester was less than 1% by weight.

The present invention will now be described more specifically referring to Examples and Comparative Examples but it should be noted that the invention is not restricted only to the following Examples. In the Examples, all per cents are by weight.

EXAMPLE 1

Glucose and linear decanoic acid chloride were reacted in pyridine solvent at a reaction temperature of 60° C. for about 30 min. to obtain a crude product of glucose decanoate.

Then, the crude product was fractionated on column chromatography (carrier: silica gel, trade name: Wakogel C-200, manufactured by Wako Junyaku Co., solvent: methanol/ethyl ether/hexane) to obtain glucose decanoate monoester, diester, triester, tetraester and pentaester respectively.

Each of the fractions obtained by the silica gel column chromatography was removed with a solvent under a reduced pressure in a rotary evaporator and then further dried in vacuum over one day to prepare a specimen. Each of the esters was confirmed to be mono-, di-, tri-, tetra- and penta-form according to NMR and gas chromatography for acetylation products respectively.

Five kinds of glucose esters fractionated as described above were mixed at various ratios shown in Table 1, and the taste and the foaming power were evaluated by the following methods.

For comparison, the taste and the foaming power were examined in the same manner as above for sucrose laurate, decyl polyglycoside, polyglycerol laurate and sorbitan laurate. The results are shown in Table 1.

Taste

Each of the samples was held as it was in mouth and the taste was evaluated.

○: tasteless or slightly tasted
X: keen bitterness or oily taste

Foaming power 10 ml of a 0.5% aqueous solution for each of the samples was taken into a 100 ml of an epton tube and the volume of foams after shaken 15 times at 40° C. was evaluated.

○: satisfactory foaming
Δ: somewhat satisfactory foaming
X: poor foaming

TABLE 1

| Surface active agent | | Blending ratio (wt %) | | | | | | | | | | |
|---|---|---|---|---|---|---|---|---|---|---|---|---|
| Glucose decanoate | monoester | 99.7 | 95 | 95 | 95 | 95.5 | 90 | | | | | |
| | diester | 0.3 | 0 | 3.5 | 4.5 | 4.5 | 5 | | | | | |
| | tri-or higher ester | 0 | 5 | 1.5 | 0.5 | 0 | 5 | | | | | |
| Sucrose laurate | monoester | | | | | | | 100 | | | | |
| | polyester | | | | | | | | 100 | | | |
| Decyl polyglycoside | | | | | | | | | | 100 | | |
| Polyglycerol laurate | | | | | | | | | | | 100 | |
| Sorbitan laurate | | | | | | | | | | | | 100 |
| Taste | | ○ | X | X | ○ | ○ | X | X | X | X | X | X |
| Foaming | | ○ | Δ | ○ | ○ | ○ | Δ | Δ | X | Δ | X | X |
| | | Example | Comparative Example | | Example | | Comparative Example | | | | | |

From the results shown in Table 1, it can be recognized that the glucose fatty acid ester according to the present invention is tasteless and can provide satisfactory foaming agent.

Similar results to those described above could also be obtained in case of using glucose octanoate and glucose laurate.

EXAMPLE 2

Glucose and linear decanoic acid chloride were reacted in pyridine solvent at a reaction temperature of 60° C. for about 30 min. to obtain a crude product of glucose decanoate.

Then, the crude product was fractionated on column chromatography (carrier: silica gel, trade name: Wakogel C-200, manufactured by Wako Junyaku Co., solvent: methanol/ethyl ether/hexane) to obtain glucose decanoate monoester and diester respectively.

In the same way, glucose octanoate monoester and diester were obtained respectively.

The thus obtained glucose esters were mixed at a weight ratio as shown in Table 2, and their foaming power and feeling of foam were evaluated respectively.

For comparison, foaming power and feeling of foams of sucrose laurate (monoester content: diester content=98:2, manufactured by Dojin Kagaku Co.) and an adduct of 9 mol of ethylene oxide to $C_{12-13}$ alcohol (trade name: Emalex, manufactured by Nippon Emulsion Co.) were evaluated.

The results are shown in Table 2.

Foaming power and feeling of foams were evaluated by the following methods.

Foaming power 10 ml of an aqueous sample solution containing a surface active agent at a concentration of 0.5% by weight was taken into a 100 ml epton tube and the volume of foams after shaking 10 times at 40° C. was evaluated by the height of foams.

Feeling of Foam 50 ml of an aqueous sample solution containing a surface active agent at a concentration of 0.5% was charged in a 100 ml sample bottle equipped with a lid. After shaking them 10 times at 40° C., the foamed sample solution was used for face cleansing and evaluated.
◯: fresh feeling
Δ: somewhat fresh feeling
X: weak fresh feeling

TABLE 2

| Glucose fatty acid ester | | Example | | | | Comparative Example | |
|---|---|---|---|---|---|---|---|
| $C_8$ | Monoester | 95.5 | 99.7 | 99.7 | 99.7 | Sucrose laurate | EO 9 mol adduct of $C_{12-13}$ alcohol |
|  | Diester | 4.5 | 0.3 | 0.3 | 0.3 |  |  |
| $C_{10}$ | Monoester | 99.5 | 99.5 | 99.5 | 99.5 |  |  |
|  | Diester | 0.5 | 0.5 | 0.5 | 0.5 |  |  |
| $C_8/C_{10}$ ratio | | 90/10 | 80/20 | 50/50 | 30/70 |  |  |
| Foam height (ml) | | 85 | 90 | 85 | 80 | 40 | 30 |
| Feeling of form | | ◯ | ◯ | ◯ | ◯ | X~Δ | X~Δ |

From the results shown in Table 2, it can be recognized that the combined use of glucose octanoate and glucose decanoate according to the present invention acts synergistically to provide excellent foaming power and feeling of foams.

EXAMPLE 3

Gargling test by 20 panellers was conducted using an aqueous mixed solution of sodium lauryl sulfate and glucose-6-monocaprate (monoester 98.7%, diester 1.2%, triester 0.1%) at the ratio shown in Table 3 and stimulative feeling during gargling and sense of incongruity remaining in the oral mucous membrane when rinsing with water after gargling were evaluated. The test results are shown in Table 3. Values in the column for the result of the evaluation in the table indicate the number of panellers who complained stimulative feeling or sense of incongruity.

TABLE 3

|  |  | No. 1 | No. 2 | No. 3 | No. 4 |
|---|---|---|---|---|---|
| Sodium lauryl sulfate (A) | | 0.5% | 0.25% | 0.17% | 0% |
| Glucose-6-monocaprate (B)* | | 0% | 0.25% | 0.33% | 0.5% |
| (A)/(B) weight ratio | | 1/0 | 1/1 | 1/2 | 0/1 |
| Result | Stimulative feeling during gargling (number of panellers) | 18 | 2 | 0 | 0 |
|  | Sense of incongruity after gargling | 15 | 1 | 0 | 0 |

TABLE 3-continued

|  | No. 1 | No. 2 | No. 3 | No. 4 |
|---|---|---|---|---|
| (number of panellers) | | | | |

*monoester: 98.7%, diester: 1.2%, triester: 0.1%

As shown in Table 3, it can be recognized that stimulation to oral mucous membrane was remarkably reduced by the combined use of sodium lauryl sulfate and glucose-6-monocaprate according to the present invention.

EXAMPLE 4

A toothpaste composition of the following formulation was prepared in the conventional manner by using the foaming agent (surface active agent) shown in Table 4. The foaming property of the toothpaste compositions was evaluated by the following method.

| Formulation of toothpaste composition | wt % |
|---|---|
| Calcium secondary phosphate | 45.0 |
| Silicic anhydride | 3.0 |
| Sodium carboxymethyl cellulose | 0.8 |
| Carrageenan | 0.2 |
| Sorbitol | 26.0 |
| Propylene glycol | 3.0 |
| Sodium saccharinate | 0.2 |
| Flavor | 1.0 |
| Foaming agent | 2.0 |
| Purified water | balance |
| Total | 100.0% |

Evaluation method for foaming property

Tooth cleaning test was conducted by five well-trained panellers using a toothpaste composition prepared by the formulation as described above and the foaming property was evaluated by the following evaluation standards.

Evaluation standards for foaming property
⊚: well foaming
◯: moderately foaming
Δ: slightly foaming
X: scarcely foaming

TABLE 4

| Surface active agent | 5 | 6 | 7 |
|---|---|---|---|
| Sodium lauryl sulfate (A) | 2.0% | 1.0% | 0.65% |
| Glucose-6-monocaprate (B)* | 0% | 1.0% | 1.35% |
| (A)/(B) weight ratio | 1/0 | 1/1 | 1/2 |
| Foaming property | ◯ | ◯ | ◯ |

*monoester: 99.7%, diester: 0.3%, triester: 0%

As apparent from the results shown in Tables 3 and 4, it can be recognized that high foaming property and weak stimulation to oral mucous membrane are shown in case of using sodium lauryl sulfate and glucose-6-monocaprate of the present invention in combination.

EXAMPLE 5

A toothpaste composition of the following formulation was prepared in the conventional manner by using the foaming agent (surface active agent) shown in Table 5. The foaming property and the taste of the toothpaste composition was evaluated by the method described later. The results are shown in Table 5.

| Formulation of toothpaste composition | (unit %) |
|---|---|
| Calcium secondary phosphate | 45.0 |
| Silicic anhydride | 3.0 |
| Sodium carboxymethyl cellulose | 0.8 |
| Carrageenan | 0.2 |
| Sorbitol | 26.0 |
| Propylene glycol | 3.0 |
| Sodium saccharinate | 0.2 |
| Flavor | 1.0 |
| Foaming agent | amount shown in Table 1 |
| Purified water | balance |
| Total | 100.0 |

Evaluation method for foaming property and taste

Tooth cleaning test was conducted by five well-trained panellers using the toothpaste composition prepared by the formulation as described above and the foaming property and the taste were evaluated by the following evaluation standards.

Evaluation standards for foaming property
- ⊚: well foaming
- ○: moderately foaming
- Δ: slight foaming
- X: scarcely foaming Evaluation standards for taste
- : satisfactory (with no bitterness)
- Δ: some bitterness
- X: keen bitterness and not usable

TABLE 5

| Surface active agent | Blending amount (%) | Foaming power | Taste |
|---|---|---|---|
| Glucose-6-monolaurate* + sodium N-lauroyl glutamate | 1.5 / 0.5 | ⊚ | ○ |
| Glucose-6-monolaurate* + sodium N-lauroyl sarcosinate | 1.5 / 0.5 | ⊚ | ○ |
| Glucose-6-monolaurate* + sodium N-lauroylmethyl-β-alaninate | 1.5 / 0.5 | ⊚ | ○ |
| N-lauroyl sarcosinate | 0.5 | X | ○ |
| Sodium N-lauroyl glutamate | 0.5 | X | ○ |
| Sodium N-lauroylmethyl-β-alaninate | 0.5 | X | ○ |

*monoester: 99%, diester: 1%, triester: 0%

As shown in Table 5, it has been recognized that the foaming property can be improved remarkably with no undesired effect on the taste by the combined use of glucose fatty acid ester of the present invention with the N-acylamino acid salt.

EXAMPLE 6

A toothpaste composition of the same formulations as in Example 5 were prepared except for using the foaming agent (surface active agent) shown in Table 6. The foaming property and the taste of the toothpaste compositions were evaluated in the same standards as those in Example 5. The results are shown in Table 6.

TABLE 6

| Surface active agent | Blending amount (%) | Foaming power | Taste |
|---|---|---|---|
| Glucose-6-monocaprate* + sodium N-lauroyl sarcosinate | 1.5 / 0.2 | ○ | ○ |
| Glucose-6-monocaprate* + sodium N-lauroyl sarcosinate | 1.5 / 0.5 | ⊚ | ○ |
| Glucose-6-monocaprate* + sodium N-lauroyl sarcosinate | 1.5 / 0.5 | ⊚ | ○ |
| Glucose-6-monocaprylate* + Sodium N-hardened tallow/coconut oil mixed fatty acid glutamate | 1.5 / 0.5 | ⊚ | ○ |

*monoester: 99%, diester: 1%, triester: 0%

As shown in Table 6, all of toothpaste compositions using glucose fatty acid ester of the present invention and N-acylamino acid salt showed satisfactory foaming property and taste.

EXAMPLE 7

A toothpaste composition of the following formulation was prepared in the conventional manner by using the foaming agent (surface active agent) shown in Table 7. The foaming property, taste and low temperature stability of the toothpaste composition was evaluated by the same method as in Example 5. The results are shown in Table 7.

| Formulation of toothpaste composition | wt % |
|---|---|
| Calcium secondary phosphate | 45.0 |
| Silicic anhydride | 3.0 |
| Sodium carboxymethyl cellulose | 0.8 |
| Carrageenan | 0.2 |
| Sorbitol | 26.0 |
| Propylene glycol | 3.0 |
| Sodium saccharinate | 0.2 |
| Flavor | 1.0 |
| Foaming agent | 2.0 |
| Purified water | balance |
| Total | 100.0% |

Stability of low temperature

Each of the toothpaste compositions thus prepared was charged in an aluminum laminated tube. After storing the tube at 0° C. for one month, the content was taken out, observed for the appearance and then evaluated by the following standards.
- ○: smooth appearance with luster
- Δ: luster was eliminated, with small amount of fine deposition
- X: a great amount of coarse deposits

TABLE 7

| Foaming agent | Comparative Example | Example | |
|---|---|---|---|
| Sodium N-lauroylmethyl taurate | 2.0% | 0.8% | 0.5% |
| Glucose-6-monocaprate* | 0% | 1.2% | 1.5% |
| Foaming property | ○ | ○ | ○ |
| Taste | Δ | ○ | ○ |
| Low temperature stability | X | ○ | ○ |

*monoester: 99%, diester: 1%, triester: 0%

As can be seen from the results shown in Table 7, the toothpaste composition was excellent in each of the foaming property, taste and low temperature stability.

EXAMPLE 8

(1) Hair smoothness during rinsing

Hairs of a head were parted in the middle into right and left halves, to each of which 3 g of a standard shampoo and a test solution shown in Table 8 were applied to foam. Then, hair smoothness upon rinsing with warm water was evaluated and judged in accordance with the following standards by 10 panellers.

⊚: more excellent in the smoothness than standard shampoo lamp and a change of color was visually judged. The evaluation standards are as shown below.

◯: no discoloration observed as compared with the product stored at room temperature Δ: slight discoloration observed as compared with the product stored at room temperature X: apparent discoloration observed as compared with the product stored at room temperature

TABLE 8

| Ingredient | | Comparative Example | | | | Example | | | | | |
|---|---|---|---|---|---|---|---|---|---|---|---|
| Glucose fatty acid ester | Glucose-6-caprate monoester* | | | | | 10 | | | | | |
| | Glucose-6-laurate monoester* | | | | | | 10 | | | | |
| | 1-ethyl-6-caprate glucose ester* | | | | | | | 10 | | | |
| | 1-ethyl-6-laurate glucose ester* | | | | | | | | 10 | | |
| | Glucose-6-cocoyl monoester* | | | | | | | | | 10 | |
| | Glucose-6-nonanic monoester* | | | | | | | | | | 10 |
| Amphoteric surface active agent | Imidazolinium betaine (R:coconut oil) | 10 | | | | 5 | | | | | |
| | Amidopropyl betaine (R:coconut oil) | | 10 | | | | 5 | | | | |
| | Alkyl betaine (R:coconut oil) | | | | | | | 5 | | | |
| | Sodium β-laurylamino propionate | | | | | | | | 5 | | |
| | Sodium lauryl diaminoethyl glycine | | | | | | | | | 5 | |
| | Lauryl dimethylamino acetic acid betaine | | | 10 | | | | | | | |
| | Alkyl dimethylamino hydroxypropyl sulfobetaine | | | | 10 | | | | | | 5 |
| Purified water | | | | | | balance | | | | | |
| Total | | 100 | 100 | 100 | 100 | 100 | 100 | 100 | 100 | 100 | 100 |
| Hair smoothness upon rinsing | | Δ | Δ | Δ | Δ | ⊚ | ⊚ | ⊚ | ⊚ | ⊚ | ⊚ |
| Color stability at 60° C. | | X | X | Δ | Δ | ◯ | ◯ | ◯ | ◯ | ◯ | ◯ |
| Color stability under xenon lamp irradiation | | X | X | X | X | ◯ | ◯ | ◯ | ◯ | ◯ | ◯ |

*monoester: 99%, diester: 1%, triester: 0%

◯: somewhat excellent in the smoothness than standard shampoo

Δ: similar to the smoothness of standard shampoo

X: inferior to the smoothness of standard shampoo

The standard shampoo used herein comprised 10% by weight of sodium polyoxyethylene lauryl ether sulfate ($\bar{p}$: 3), 3% by weight of coconut oil fatty acid diethanol amide, 1% by weight of sodium sulfate and the balance of water.

(2) Color stability evaluation

The test solution shown in Table 8 was stored for one month at 60° C. or under the irradiation of a xenone Then, shampoo compositions having the formulation shown in Table 9 and hair smoothness upon rinsing and color stability were evaluated and judged. The results are shown in Table 9. As can be seen from the result of the table, a sufficient effect could be obtained in any of the compositions.

TABLE 9

| | | Example | | | | |
|---|---|---|---|---|---|---|
| Glucose fatty acid ester | Glucose-6-caprate monoester* | 10 | 5 | 12 | 10 | 10 |
| | Glucose-6-laurate monoester* | | | 3 | | |
| | 1-ethyl-6-caprate glucose ester* | | 5 | | | |
| | 1-ethyl-6-laurate glucose ester* | | | | 5 | |
| Amphoteric surface active agent | Imidazolinium betaine (R: coconut oil) | 5 | | | | |
| | Amidopropyl betaine (R: coconut oil) | | 5 | 5 | 5 | 5 |
| Sodium α-olefin sulfonate | | | | 2 | | |
| Sodium polyoxyethylene alkyl ether sulfate ($C_{12}/C_{13}$ = 1/1, $\bar{p}$ = 3) | | | | | | 2 |
| Quarternary nitrogen-containing cellulose ether (nitrogen content: 2.0%, molecular weight: 100,000) | | 0.5 | 0.7 | | | 0.5 |
| Copolymer of dimethylallyl ammonium chloride and acrylamide (MERQUAT 550, manufactured by Merck Co.) | | | | | 0.1 | |
| EDTA | | | | 0.05 | | |
| Ethyleneglycol distearate | | 1.0 | | | | 1.0 |
| Trimethylammonium chloride ($C_{16}$~$C_{18}$) | | | | | | 0.1 |
| Coconut oil fatty acid diethanolamide | | 2 | 3 | 2.5 | 1.5 | 3 |
| Ethanol | | | 0.4 | | | |
| Parabene | | | 0.1 | | | |
| Benzoic acid salt | | 1 | 1 | 1 | 1 | 1 |
| Perfume | | trace | trace | trace | trace | trace |
| Dye | | trace | trace | trace | trace | trace |
| Purified water | | | | balance | | |
| Total | | 100 | 100 | 100 | 100 | 100 |
| Hair smoothness during rinsing | | ⊚ | ⊚ | ⊚ | ⊚ | ⊚ |
| Color stability at 60° C. | | ◯ | ◯ | ◯ | ◯ | ◯ |
| Color stability under xenon lamp irradiation | | ◯ | ◯ | ◯ | ◯ | ◯ |

*monoester: 99%, diester: 1%, triester: 0%

EXAMPLE 9

A few drops of a test solution shown in Table 10 was taken on one hand and a standard specimen (a 15% aqueous solution of the following anionic surface active agent (1)) was taken on the other hand, and the degree of slimy feeling therebetween was compared by 20 test panellers. The results are shown in the table. The evaluation standards are as shown below.
- ○: less slimy than the standard specimen (slimy feeling was scarcely felt)
- Δ: somewhat slimy feeling as that of standard specimen (some slimy feeling)
- X: more slimy feeling than that of standard specimen (slimy feeling was felt)

There were given score "1" if the test solution was less slimy than that of the standard specimen, score "0" if the slimy feeling was identical and score "−1" if the standard specimen was less slimy than the test solution. Then, for the total scores by the 20 panellers, score of 5 or greater was represented as "○", score of from more than −5 to less than 5 as "Δ" and score of −5 or less as "X".

The surface active agent used herein was as shown below.

Anionic surface active agent (1):
  Na-$C_{14}$-α-olefin sulfonate
Anionic surface active agent (2):
  Sodium polyoxyethylene (3) lauryl ether sulfate
Amphoteric surface active agent (1):
  Amidopropyl betaine (R: coconut oil)
Amphoteric surface active agent (2):
  Imidazoline type amphoteric surface active agent (R: coconut oil)
Cationic surface active agent
  $C_{16-18}$ trimethylammonium chloride
Nonionic surface active agent:
  Coconut oil fatty acid diethanol amide From the results shown in Table 10, it has been confirmed that slimy feeling of the anionic surface active agent was eliminated by blending the glucose fatty acid ester with 11 to 20 carbon atoms in the acyl group according to the present invention.

TABLE 10

| Ingredient (%) | No. 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| Glucose-6-cocoyl monoester* | | 5 | | | 5 | 10 | 10 | 10 | 10 | 5 | 3 | 0.5 | 30 | 10 | 20 | |
| Glucose-6-palmitoyl monoester* | | | 5 | | | | | | | | | | | | | |
| 1-ethyl-6-cocoyl glucose ester* | | | | 5 | | | | | | | | | | | | |
| Anionic surface active agent (1) | 15 | 15 | 15 | 15 | | | | 10 | 15 | 12 | 10 | 13 | 15 | 5 | 30 | 2 |
| Anionic surface active agent (2) | | | | | 15 | 15 | 10 | | | | | | | | | |
| Amphoteric surface active agent (1) | | | | | | | 5 | | | | 5 | 2 | | | | |
| Amphoteric surface active agent (2) | | | | | | | | | 5 | | | | | | | |
| Cationic surface active agent | | | | | | | | | | 1 | | | | 1 | | |
| Nonionic surface active agent | | | | | | | | | | | 5 | 2 | 3 | | | |
| Purified water | | | | | | | balance | | | | | | | | | |
| Total | 100 | 100 | 100 | 100 | 100 | 100 | 100 | 100 | 100 | 100 | 100 | 100 | 100 | 100 | 100 | 100 |
| Slimy feeling | Δ | ○ | ○ | ○ | X | ○ | ○ | ○ | ○ | ○ | ○ | ○ | ○ | ○ | ○ | ○ |

*monoester: 99%, diester: 1%, triester: 0%.

EXAMPLE 10

Detergent compositions having the formulations shown in Table 11 were prepared to evaluate slimy feeling. The results are shown in Table 11.

Evaluation method for Slimy Feeling

A hand was dipped in a 10% aqueous solution of the composition and evaluated by means of panellers' touch based on the following standards. The scores were mean values for five or more panellers.
- 5: no slimy feeling
- 4: less slimy feeling
- 3: slimy feeling
- 2: rather slimy
- 1: remarkably slimy

TABLE 11

| Ingredient (%) | No. 1 | No. 2 | No. 3 | No. 4 | No. 5 | No. 6 | No. 7 | No. 8 | No. 9 | No. 10 | No. 11 | No. 12 | No. 13 | No. 14 | No. 15 | No. 16 |
|---|---|---|---|---|---|---|---|---|---|---|---|---|---|---|---|---|
| $C_6$ glucose ester*2 | 9 | | | | | | | | | | | 10 | 10 | 10 | 10 | |
| $C_8$ glucose ester*2 | | 9 | | | 5 | 10 | 15 | 20 | | | | | | | | |
| $C_{10}$ ethyl glucose ester*2 | | | 9 | | | | | | 20 | 30 | | | | | | |
| $C_{22}$ glucose ester*2 | | | | 9 | | | | | | | | | | | | |
| Sodium $C_{11,13}$ alkyl sulfate*3 | | | | | | | | | | | 10 | | | | | |
| Sodium $C_{12,13}$ alkyl sulfate*4 | 5 | 5 | 5 | 5 | | | | | | | | | | | | 10 |
| Sodium $C_{10-18}$ α-olefin sulfonate | | | | | 0.5 | 0.5 | 0.5 | 0.5 | | | | | 10 | | 5 | |
| Sodium $C_{12}$ alaninate | | | | | | | | | 5 | 5 | | | | 10 | | |
| Sodium $C_{15}$ alkyl sulfonate | | | | | | | | | | | | | | | 10 | |
| Water | | | | | | | balance | | | | | | | | | |
| Total | 100 | 100 | 100 | 100 | 100 | 100 | 100 | 100 | 100 | 100 | 100 | 100 | 100 | 100 | 100 | 100 |
| Slimy feeling after washing | 4 | 4 | 4 | 4 | 5 | 5 | 5 | 5 | 5 | 5 | 4 | 4 | 4 | 4 | 2 | 2 |

*1 Specimen Nos. 1-14 are Examples, other specimens are Comparative Examples
*2 Fatty acid glucose or glucoside ester with the carbon atoms indicated in table (monoester: 99%, diester: 1%, triester: 0%)
*3 Higher alcohol with 50% or more of straight chain rate composed mainly of $C_{12,13}$ was used.
*4 Higher alcohol with 70% or more of straight chain rate composed mainly of $C_{12,13}$ was used.

EXAMPLE 11

Detergent compositions having the formulations shown in Tables 12-14 were prepared to evaluate slimy feeling in the same manner as in Example 10. The results are shown in Tables 12-14.

TABLE 12

| Composition (wt %) | | No. 1 | No. 2 | No. 3 | No. 4 | No. 5 | No. 6 | No. 7 | No. 8 | No. 9 |
|---|---|---|---|---|---|---|---|---|---|---|
| $C_6$ glucose ester*1 | | 10 | | | | | 15 | | | |
| $C_8$ glucose ester*1 | | | 10 | 10 | | | | 20 | | 5 |
| $C_{10}$ glucose ester*1 | | | | | 10 | | | | 30 | |
| $C_{12}$ glucose ester*1 | | | | | | 10 | | | | |
| Coconut oil fatty acid diethanol amide | | 5 | 5 | | | | | | | |
| Higher alcohol polyoxyethylene ether | ($\bar{p}$ = 12)*2 | | | 10 | 10 | | | | | |
| | ($\bar{p}$ = 15)*2 | 5 | 5 | | | | 10 | | | |
| | ($\bar{p}$ = 15)*3 | | | | | | 10 | | | |
| $C_{10-14}$ secondary alcohol polyoxyethylene ether | ($\bar{p}$ = 7) | | | | | | | 5 | | |
| | ($\bar{p}$ = 9) | | | | | | | | 0.5 | |
| | ($\bar{p}$ = 12) | | | | | | 10 | | | |
| | ($\bar{p}$ = 15) | | | | | | | | | 10 |
| water | | | | | | balance | | | | |
| Total | | 100 | 100 | 100 | 100 | 100 | 100 | 100 | 100 | 100 |
| Slimy feeling after washing | | 4 | 4 | 5 | 5 | 4 | 5 | 5 | 5 | 4 |

*1 monoester: 99%, diester 1%, triester 0%
*2 Alcohol with 50 wt % or more of straight chain rate composed mainly of $C_{11,13}$ was used as higher alcohol.
*3 Alcohol with 70 wt % or more of straight chain rate composed mainly of $C_{11,13}$ was used as higher alcohol.
*4 $C_{10-14}$ secondary alcohol with 90 wt % of straight chain rate was used.

TABLE 13

| Ingredient (%) | | No. 1 | No. 2 | No. 3 | No. 4 | No. 5 | No. 6 | No. 7 | No. 8 |
|---|---|---|---|---|---|---|---|---|---|
| $C_6$ glucose ester*2 | | | 8 | | | | | | |
| $C_8$ ethyl glucose ester*2 | | 5 | | 8 | | | | 30 | |
| $C_{10}$ glucose ester*2 | | | | | 8 | | 20 | | |
| $C_{12}$ glucose ester*3 | | | | | | 8 | | | |
| Alkylamine oxide*3 | A | 0.5 | | 3 | 3 | | 5 | | 3 |
| | B | | 3 | | | 8 | | 10 | |
| Sodium higher alcohol polyoxyethylene sulfate ($\bar{p}$ = 3)*4 | A | | 5 | | | 5 | 10 | | 10 |
| | B | | | | | | | | |
| water | | | | | balance | | | | |
| Total | | 100 | 100 | 100 | 100 | 100 | 100 | 100 | 100 |
| Slimy feeling after washing | | 5 | 5 | 5 | 5 | 5 | 4 | 5 | 2 |

*1 Specimen Nos. 1-7 are Examples, No. 8 is Comparative Example.
*2 Fatty acid glucose or glucoside ester with the number of carbon atoms in the table (monoester: 99%, diester 1%, triester 0%)
*3 Alkylamine oxide:
A: $C_{12}$ dimethylamine oxide with 90% or more of straight chain rate at $C_{12}$ alkyl group.
B: $C_{14}$ diethylamine oxide with 40 to 90% of straight chain rate at $C_{14}$ alkyl group.
*4 Sodium higher alcohol polyoxyethylene sulfate ($\bar{p}$ = 3)
A: Alcohol with 70% or more of straight chain rate composed of 90 wt % or more of $C_{12,13}$ was used as higher alcohol. (average addition mol number of polyoxyethylene = 3)
B: Alcohol with 50% or more of straight chain rate composed mainly of $C_{11,13}$ was used as higher alcohol (average addition mol number of polyoxyethylene = 3)

TABLE 14

| Ingredient (%) | No. 1 | No. 2 | No. 3 | No. 4 | No. 5 | No. 6 | No. 7 |
|---|---|---|---|---|---|---|---|
| $C_6$ glucose ester*1 | 10 | | | | | | |
| $C_8$ ethyl glucose ester*1 | | 10 | | | 5 | 20 | 30 |
| $C_{10}$ glucose ester*1 | | | 10 | | | 20 | |
| $C_{12}$ glucose ester*1 | | | | 10 | | | |
| $C_{12}$ fatty acid diethanol amide*2 | 10 | 10 | 10 | 10 | 1 | 20 | 15 |
| Ethanol | 2 | 5 | | 2 | 5 | 3 | |
| Sodium p-toluene sulfonate | | | 1.5 | 3 | 3 | 1.5 | 2 |
| water | | | | balance | | | |
| Total | 100 | 100 | 100 | 100 | 100 | 100 | 100 |
| Slimy feeling of washing liquid | 5 | 5 | 5 | 5 | 5 | 5 | 5 |

*1 Fatty acid ester with the number of carbon atoms indicated in the table. Monoester: 99%, diester: 1%, triester: 0%
*2 $C_{12}$ fatty acid diethanol amide: Amide comprised of fatty acid and diethanol amine, 85% by weight of the fatty acid radical of the fatty acid being occupied by $C_{12}$ fatty acid radical.

EXAMPLE 12

Detergent compositions having the formulations shown in Table 15 were prepared to evaluate the state of forming the films. The results are shown in Table 15.

Evaluation method for the formation of films 20 ml of a liquid detergent was sampled into a 30 ml of sample beaker, left under the conditions of 20° C. and 70% RH for 12 hours, the surface state of the liquid was observed and the evaluation was conducted in the following.

Formation of films

A: No films on the surface
B: Films formed at a portion of the surface
C: Thin films formed over the entire surface
D: Thick films formed over the entire surface

TABLE 15

| Ingredient (%) | No. 1 | No. 2 | No. 3 | No. 4 | No. 5 | No. 6 | No. 7 | No. 8 |
|---|---|---|---|---|---|---|---|---|
| $C_6$ glucose ester*1 | 10 | | | | | | | |

TABLE 15-continued

| Ingredient (%) | | No. 1 | No. 2 | No. 3 | No. 4 | No. 5 | No. 6 | No. 7 | No. 8 |
|---|---|---|---|---|---|---|---|---|---|
| $C_8$ glucose ester*[1] | | 5 | | 20 | 30 | | | | |
| Methyl $C_{10}$ glucose ester*[1] | | | | | | 10 | 10 | | |
| $C_{12}$ glucose ester*[1] | | | | | | | | 10 | 10 |
| Polyethylene glycol | Molecular weight 200 | | | | 1 | | | | |
| | Molecular weight 400 | | | | | | 1 | | |
| | Molecular weight 800 | | | | | | | 1 | |
| | Molecular weight 1000 | 0.5 | 1 | 3 | 5 | | | | |
| | Molecular weight 7000 | | | | | | | | 1 |
| Sodium $C_{12,13}$ alkyl polyoxyethylene sulfate | ($\bar{p}$ = 3) | 5 | | | | | | 10 | 10 |
| | ($\bar{p}$ = 4) | | 5 | 10 | | 10 | 10 | | |
| | ($\bar{p}$ = 5) | | | | 10 | | | | |
| Sodium $C_{10-12}$ α-olefin sulfonate | | 3 | 3 | 3 | 3 | 3 | 3 | 3 | 3 |
| sodium toluene sulfonate | | 2 | 2 | 2 | 2 | 2 | 2 | 2 | 2 |
| Ethanol | | 3 | 3 | 3 | 3 | 3 | 3 | 3 | 3 |
| Sodium benzoate | | 1 | 1 | 1 | 1 | 1 | 1 | 1 | 1 |
| Fragrance | I | 0.2 | 0.2 | 0.2 | | 0.2 | 0.2 | | |
| | II | | | | 0.2 | | | 0.2 | 0.2 |
| Dye | | 0.01 | 0.01 | 0.01 | 0.01 | 0.01 | 0.01 | 0.01 | 0.01 |
| $C_{12}$ diethanol amide | | 2 | 2 | 2 | 2 | 2 | 2 | 2 | 2 |
| $C_{12}$ alkylamine oxide | | 3 | 3 | 3 | 3 | 3 | 3 | 3 | 3 |
| water | | | | | bal | ance | | | |
| | Total | 100 | 100 | 100 | 100 | 100 | 100 | 100 | 100 |
| Film formation | | B | A | A | A | A | A | A | A |

*[1] Fatty acid glucose or glucoside ester with the number of carbon atoms indicated in the table. Monoester: 99%, diester: 1%, triester: 0%
*[2] Compositions for fragrance I and II are as follows.

| Ingredient | (parts by weight) |
|---|---|
| Flavor (I): | |
| Anise oil | 1 |
| Calmus oil | 1 |
| Camomile oil | 1 |
| Coriander oil | 1 |
| Eucalyptus oil | 2 |
| Gingergrass oil | 1 |
| Mandarin oil | 1 |
| Spearmint oil | 1 |
| Parseley oil | 1 |
| Pimenta oil | 1 |
| Star anise oil | 1 |
| Worm-wood oil | 1 |
| Orris oil | 1 |
| Orange oil | 5 |
| Grapefruit oil | 2 |
| Tangerine oil | 1 |
| Bonzoin oil | 1 |
| Pine oil | 2 |
| Angelica oil | 1 |
| Caraway oil | 1 |
| Cinnamon oil | 1 |
| Deyl oil | 1 |
| Fennel oil | 1 |
| Laurel leaf oil | 1 |
| Tangerine oil | 1 |
| Peppermint oil | 2 |
| Patchouli oil | 2 |
| Rosemary oil | 1 |
| Ylang Ylang oil | 2 |
| Ho oil | 2 |
| Lemon oil | 5 |
| Yuzu oil | 1 |
| Tansy oil | 1 |
| Bois de Rose oil | 2 |
| Sandalwood oil | 2 |
| Basil oil | 1 |
| Cassia oil | 1 |
| Citronella oil | 1 |
| Elemi oil | 1 |
| Galbanum oil | 1 |
| Lavender oil | 2 |
| Peppermint oil | 2 |
| Neroli oil | 1 |
| Perilla oil | 1 |
| Camphor oil | 2 |
| Thyme oil | 1 |
| Rose oil | 1 |
| Aromois oil | 1 |
| Lime oil | 2 |

-continued

| Ingredient | (parts by weight) |
|---|---|
| Sudachi oil | 1 |
| Oak moss oil | 2 |
| Cederwood oil | 2 |
| Tonka beans oil | 1 |
| Bergamot oil | 5 |
| Celery oil | 1 |
| Clove oil | 1 |
| Estragon oil | 1 |
| Geranium oil | 1 |
| Lemongrass oil | 1 |
| Nutmeg oil | 1 |
| Petigrain oil | 1 |
| Clary sage oil | 1 |
| Wintergreen oil | 1 |
| Tomato leaf absolute | 1 |
| Mandrain oil | 2 |
| Lavandin oil | 2 |
| Orange flower oil | 1 |
| Vetiver oil | 1 |
| Perfume (II): | |
| Aldehyde C-7 | 0.5 |
| Aldehyde C-8 | 0.5 |
| Aldehyde C-9 | 0.5 |
| Aldehyde C-10 | 0.5 |
| Aldehyde C-11 | 0.5 |
| Aldehyde C-12 MNA | 0.5 |
| γ-undecalactone | 1.0 |
| Ethyl methyl phenyl glycidate | 1.0 |
| p-methyl-β-ethylnyl glycidate | 1.0 |
| α-n-amyl cinnamic aldehyde | 2.5 |
| Anethol | 1.0 |
| Anisaldehyde | 1.0 |
| Anisalcohol | 1.0 |
| p-tert-butyl cyclohexyl acetate | 2.5 |
| l-bornyl acetate | 1.0 |
| Cedryl acetate | 1.0 |
| 1,8-cineol | 1.0 |
| Citral | 2.5 |
| Citronellal | 0.5 |
| Citronellol | 2.5 |
| Citronellyl acetate | 2.5 |
| Cinnamic aldehyde | 1.0 |
| Cumarin | 1.0 |
| Cyclamen aldehyde | 2.5 |
| Damascone | 0.5 |
| Dimethyl anthranilate | 0.5 |
| Dipentene | 0.5 |
| Diphenyl oxide | 0.5 |
| Ethyl acetate | 0.5 |
| Ethyl anthranilate | 0.5 |

-continued

| Ingredient | (parts by weight) |
|---|---|
| Ethyl vanillin | 0.5 |
| Eugenol | 1.0 |
| Bicyclohydrohomofernecyl oxide | 2.5 |
| Galacsolide | 2.5 |
| Geraniol | 2.5 |
| Geranyl acetate | 2.5 |
| Helional | 1.0 |
| Heliotropine | 1.0 |
| Ionon | 2.5 |
| α-n-hexyl cinnamic aldehyde | 2.5 |
| cis-3-hexanol | 0.5 |
| Hyacinth aldehyde | 0.5 |
| Hydrotropa aldehyde | 0.5 |
| Iso E super | 1.0 |
| Isoeugenol | 1.0 |
| Lilial | 2.5 |
| Limonene | 2.5 |
| Linalool | 2.5 |
| Linalool oxide | 0.5 |
| Linalyl acetate | 2.5 |
| Lyral | 2.5 |
| l-menthol | 0.5 |
| Methyl anthranilate | 1.0 |
| Methyl ionone | 2.5 |
| Methylmethyl anthranilate | 0.5 |
| Musk T | 2.5 |
| Mirack aldehyde | 0.5 |
| Nerol | 0.5 |
| Phenyl ethyl acetate | 2.5 |
| β-phenyl ethyl alcohol | 2.5 |
| Bornyl methoxy cyclohexanol | 2.5 |
| Rosephenone | 0.5 |
| Styrallyl acetate | 0.5 |
| α-terpineol | 2.5 |
| Terpinyl acetate | 2.5 |
| Tetrahydrolinalool | 1.0 |
| Tetrahydro muguol | 1.0 |
| Tonalid | 1.0 |
| Vanillin | 0.5 |
| Belt fix | 2.5 |

Blending Examples of the surface active agent according to the present invention are shown below.

| Blending Example 1 (Toothpaste) | |
|---|---|
| Glucose octanoate | 1.5% |
| Calcium hydrogen phosphate | 15 |
| Silica | 15 |
| Sorbitol | 30 |
| Sodium carboxymethyl cellulose | 1 |
| Flavor and coloring agent | appropriate amount |
| Water | balance |
| Total | 100.0% |
| Blending Example 2 (Kitchen detergent) | |
| Glucose octanoate | 10% |
| Alcohol ethoxylate sulfate (Na salt) | 10 |
| Amine oxide | 5 |
| Perfume and dye | appropriate amount |
| Water | balance |
| Total | 100.0% |
| Blending Example 3 (Shampoo) | |
| Glucose ester No. 1 | 10.5% |
| Sodium lauryl sulfate | 3.5 |
| Cocoyl diethanol amide | 2.0 |
| Sodium sulfate | 1.5 |
| Perfume and dye | appropriate amount |
| Water | balance |
| Total | 100.0% |
| Glucose ester No. 1 | |
| Glucose monooctanoate | 90% |
| Glucose monodacanoate | 10% |
| Blending Example 4 (Toothpaste) | |
| Calcium secondary phosphate dihydrate | 45.0% |
| Glycerol | 5.0 |
| Sorbitol | 15.0 |
| Sodium carboxymethyl cellulose | 1.0 |
| Glucose ester No. 2 | 1.5 |
| Flavor and sweetener | appropriate amount |
| Water | balance |
| Total | 100.0% |
| Glucose ester No. 2 | |
| Glucose monooctanoate | 80% |
| Glucose monodecanoate | 20% |
| Blending Example 5 (Liquid soap) | |
| Glucose ester No. 3 | 20.0% |
| Sodium lauryl sulfate | 10.0 |
| Perfume and emulsifying agent | appropriate amount |
| Water | balance |
| Total | 100.0% |
| Glucose ester No. 3 | |
| Glucose monooctanoate | 79% |
| Glucose dioctanoate | 1% |
| Glucose monodecanoate | 19.5% |
| Glucose didecanoate | 0.5% |
| Blending Example 6 (Vegetable tableware detergent) | |
| LES | 20.0% |
| Glucose ester No. 4 | 10.0 |
| Lauryl alkanol amide | 5.0 |
| Perfume | appropriate amount |
| Water | balance |
| Total | 100.0% |
| Glucose ester No. 4 | |
| Glucose monooctanoate | 85% |
| Glucose monodecanoate | 15% |
| Blending Example 7 (Toothpaste) | |
| Aluminum hydroxide | 40.0% |
| Silicic anhydride | 2.0 |
| Propylene glycol | 3.0 |
| Sorbitol | 26.0 |
| Sodium alginate | 1.0 |
| Sodium saccharinate | 0.2 |
| Glucose-5-monolaurate | 0.7 |
| Sodium lauryl sulfate | 0.7 |
| Flavor | 1.0 |
| Preservative | trace |
| Purified water | balance |
| Total | 100.0% |
| Blending Example 8 (Toothpaste) | |
| Calcium secondary phosphate | 45.0% |
| Silicic anhydride | 3.0 |
| Sodium carboxymethyl cellulose | 1.0 |
| Carrageenan | 0.2 |
| Propylene glycol | 3.0 |
| Sorbitol | 26.0 |
| Sodium saccharinate | 0.2 |
| Sodium monofluorophosphate | 0.76 |
| Glucose-6-monolaurate | 1.0 |
| Sodium lauryl sulfate | 0.5 |
| Flavor | 1.0 |
| Preservative | trace |
| Purified water | balance |
| Total | 100.0% |
| Blending Example 9 (Toothpaste) | |
| Calcium secondary phosphate | 45.0% |
| Silicic anhydride | 3.0 |
| Aluminum oxide | 1.0 |
| Propylene glycol | 3.0 |
| Sorbitol | 25.0 |
| Sodium carboxymethyl cellulose | 0.8 |
| Carrageenan | 0.3 |
| Sodium saccharinate | 0.2 |
| Glucose-6-monocaprate | 1.0 |
| Sodium lauryl sulfate | 0.5 |
| Arantoin chlorohydroxy aluminum | 0.1 |
| Flavor | 1.0 |
| Preservative | trace |
| Purified water | balance |
| Total | 100.0% |

Blending Example 10 (Toothpaste)

| | |
|---|---|
| Zirconosilicate | 15.0% |
| Silicic anhydride | 2.0 |
| Polyethylene glycol 400 | 3.0 |
| Sorbitol | 60.0 |
| Sodium carboxymethyl cellulose | 1.4 |
| Sodium saccharinate | 0.2 |
| Glucose-6-monocaprate | 1.5 |
| Sodium lauryl sulfate | 0.5 |
| $\beta$-glycyrrhetinic acid | 0.01 |
| Tocopherol acetate | 0.1 |
| Flavor | 1.0 |
| Coloring agent | trace |
| Purified water | balance |
| Total | 100.0% |

Blending Example 11 (Toothpaste)

| | |
|---|---|
| Aluminosilicate | 20.0% |
| Glycerol | 15.0 |
| Sorbitol | 40.0 |
| Polyethylene glycol 400 | 4.0 |
| Sodium carboxymethyl cellulose | 1.2 |
| Sodium saccharinate | 0.2 |
| Glucose-6-monocaprate | 1.0 |
| Sodium lauryl sulfate | 0.5 |
| Flavor | 1.0 |
| Coloring agent | trace |
| Purified water | balance |
| Total | 100.0% |

Blending Example 12 (Toothpaste)

| | |
|---|---|
| Calcium carbonate (heavy) | 30.0% |
| Calcium carbonate (light) | 15.0 |
| Propylene glycol | 3.0 |
| Sorbitol | 30.0 |
| Sodium carboxymethyl cellulose | 1.0 |
| Sodium saccharinate | 0.1 |
| Tranexamic acid | 0.1 |
| Glucose-6-monocaprate | 1.5 |
| Sodium myristyl sulfate | 0.5 |
| Flavor | 1.0 |
| Preservative | trace |
| Purified water | balance |
| Total | 100.0% |

Blending Example 13 (Toothpower)

| | |
|---|---|
| Calcium secondary phosphate | 35.0% |
| Calcium carbonate | 40.0 |
| Glycerol | 10.0 |
| Sodium carboxymethyl cellulose | 0.3 |
| Sodium saccharinate | 0.2 |
| Glucose-6-monolaurate | 1.0 |
| Sodium lauryl sulfate | 0.5 |
| Flavor | 1.5 |
| Purified water | balance |
| Total | 100.0% |

Blending Example 14 (Mouthwash)

| | |
|---|---|
| Ethanol | 10.0% |
| Glycerol | 10.0 |
| Sorbitol | 5.0 |
| Citric acid | 0.1 |
| Sodium citrate | 0.4 |
| Sodium saccharinate | 0.05 |
| Glucose-6-monocaprylate | 1.0 |
| Sodium lauryl sulfate | 0.5 |
| Flavor | 1.0 |
| Purified water | balance |
| Total | 100.0% |

Blending Example 15 (Toothpaste)

| | |
|---|---|
| Aluminum hydroxide | 40.0% |
| Silicic anhydride | 2.0 |
| Propylene glycol | 3.0 |
| Sorbitol | 15.0 |
| Glycerol | 15.0 |
| Sodium alginate | 1.0 |
| Sodium saccharinate | 0.2 |
| Glucose-6-monolaurate | 1.5 |
| Sodium N-lauroyl glutamate | 0.5 |
| Flavor | 1.0 |
| Preservative | trace |
| Purified water | balance |
| Total | 100.0% |

Blending Example 16 (Toothpaste)

| | |
|---|---|
| Aluminum silicate | 20.0% |
| Glycerol | 15.0 |
| Sorbitol | 40.0 |
| Polyethylene glycol 400 | 4.0 |
| Sodium carboxymethyl cellulose | 1.2 |
| Sodium saccharinate | 0.2 |
| Glucose-6-monocaprate | 1.0 |
| Sodium N-lauroyl sarcosinate | 0.5 |
| Flavor | 1.0 |
| Coloring agent | slight amount |
| Purified water | balance |
| Total | 100.0% |

Blending Example 17 (Toothpaste)

| | |
|---|---|
| Calcium carbonate (heavy) | 30.0% |
| Calcium carbonate (light) | 15.0 |
| Propylene glycol | 3.0 |
| Sorbitol | 30.0 |
| Sodium carboxymethyl cellulose | 1.0 |
| Sodium saccharinate | 0.1 |
| Tranexamic acid | 0.1 |
| Glucose-6-monocaprylate | 1.5 |
| Sodium N-myristoylmethyl--alanine | 0.5 |
| Flavor | 1.0 |
| Preservative | trace |
| Purified water | balance |
| Total | 100.0% |

Blending Example 18 (Toothpaste)

| | |
|---|---|
| Calcium secondary phosphate | 45.0% |
| Silicic anhydride | 3.0 |
| Aluminum oxide | 1.0 |
| Propylene glycol | 3.0 |
| Sorbitol | 25.0 |
| Sodium carboxymethyl cellulose | 0.8 |
| Carrageenan | 0.3 |
| Sodium saccharinate | 0.2 |
| Glucose-6-monocaprate | 1.0 |
| Sodium N-lauroyl sarcosinate | 0.5 |
| Arantoin chlorohydroxy aluminum | 0.1 |
| Flavor | 1.0 |
| Preservative | trace |
| Purified water | balance |
| Total | 100.0% |

Blending Example 19 (Toothpaste)

| | |
|---|---|
| Zirconosilicate | 15.0% |
| Silicic anhydride | 2.0 |
| Polyethylene glycol 400 | 3.0 |
| Sorbitol | 60.0 |
| Sodium carboxymethyl cellulose | 1.4 |
| Sodium saccharinate | 0.2 |
| Glucose-6-monocaprylate | 1.5 |
| Sodium N-lauroylmethyl-$\beta$-alanine | 0.5 |
| $\beta$-glycyrretic acid | 0.01 |
| Tocopherol acetic acid | 0.1 |
| Flavor | 1.0 |
| Coloring agent | trace |
| Purified water | balance |
| Total | 100.0% |

Blending Example 20 (Toothpowder)

| | |
|---|---|
| Calcium secondary phosphate | 35.0% |
| Calcium carbonate | 40.0 |
| Glycerol | 10.0 |
| Sodium carboxymethyl cellulose | 0.3 |
| Sodium saccharine | 0.2 |
| Glucose-6-monolaurate | 1.0 |
| Sodium N-myristoyl sarcosinate | 0.5 |
| Flavor | 1.5 |
| Purified water | balance |
| Total | 100.0% |

Blending Example 21 (Mouthwash)

| | |
|---|---|
| Ethanol | 10.0% |
| Glycerol | 10.0 |
| Sorbitol | 5.0 |
| Citric acid | 0.1 |
| Sodium citrate | 0.4 |
| Sodium saccharinate | 0.05 |
| Glucose-6-monocaprylate | 1.0 |
| Sodium N-lauryol sarcosinate | 0.5 |
| Flavor | 1.0 |

-continued

| | |
|---|---|
| Purified water | balance |
| Total | 100.0% |

Blending Example 22 (Toothpaste)

| | |
|---|---|
| Aluminum hydroxide | 45.0% |
| Sodium carboxymethyl cellulose | 0.8 |
| Carrageenan | 0.2 |
| Sorbitol | 26.0 |
| Propylene glycol | 3.0 |
| Sodium saccharinate | 0.2 |
| Sodium N-myristoyl taurine | 1.5 |
| Glucose-6-monolaurate | 3.0 |
| Flavor | 1.0 |
| Preservative | trace |
| Purified water | balance |
| Total | 100.0% |

Blending Example 23 (Mouthwash)

| | |
|---|---|
| Ethanol | 10.0% |
| Glycerol | 15.0 |
| Citric acid | 0.1 |
| Sodium citrate | 0.4 |
| Sodium saccharinate | 0.05 |
| Sodium N-lauroylmethyl taurine | 0.5 |
| Glucose-6-monocaprylate | 2.0 |
| Flavor | 1.0 |
| Purified water | balance |
| Total | 100.0% |

Blending Example 24 (Shampoo)

| | |
|---|---|
| Glucose-6-cocoyl monoester | 5.0% |
| Glucose-6-heptanoate monoester | 5.0 |
| Sodium polyoxyethylene lauryl ether sulfate | 5.0 |
| Alkanol amide | 5.0 |
| Lanorine derivative | 1.0 |

-continued

| | |
|---|---|
| EDTA | 0.2 |
| Ethanol | 0.5 |
| Preservative | 1.0 |
| Perfume | 0.5 |
| Dye | trace |
| Purified water | balance |
| Total | 100.0% |

Blending Example 25 (Dish-wash detergent)

| | |
|---|---|
| Glucose-6-cocoyl monoester | 5.0% |
| Sodium polyoxyethylene lauryl ether sulfate | 10.0 |
| Triethanol amine lauryl sulfate | 5.0 |
| Alkanol amide | 3.0 |
| Glycol distearate | 1.0 |
| Propylene glycol | 0.2 |
| Benzoic acid | 1 |
| Perfume | 0.5 |
| Dye | trace |
| Purified water | balance |
| Total | 100.0% |

BLENDING EXAMPLE 26

Liquid dish-wash detergents having the formulations shown in Table 16 were prepared. They have no slimy feeling and good rinsing property.

TABLE 16

| Ingredient (%) | No. 1 | No. 2 | No. 3 | No. 4 | No. 5 |
|---|---|---|---|---|---|
| $C_{10}$ glucose ester | 20 | 20 | 20 | 20 | 20 |
| Sodium higher alcohol polyoxyethylene sulfate (chain linearity: 40%, $\bar{p}$ = 5) | | | | | 5 |
| Sodium $C_{11}$, $C_{13}$ alkylsulfate | 5 | | | | |
| Sodium $C_{10-18}$ α-olefin sulfonate | | 5 | | | |
| N-lauroyl glutamate | | | 5 | | |
| Sodium octenyl succinate | | | | 5 | |
| Polyoxyethylene $C_{12}$ alkyl ether ($\bar{p}$ = 7) | | | | | 10 |
| Keratin hydrolysis product (average molecular weight 1000) | 0.1 | 0.1 | 0.1 | 0.1 | 0.1 |
| Sodium benzoate | 2 | 2 | 2 | 2 | 2 |
| Sodium p-toluene sulfonate | 4 | 4 | 4 | 4 | 4 |
| Ethanol | 7 | 7 | 7 | 7 | 7 |
| Alkanolamide | 2 | 2 | 2 | 2 | 2 |
| Perfume | 0.4 | 0.4 | 0.4 | 0.4 | 0.4 |
| Dye | 0.01 | 0.01 | 0.01 | 0.01 | 0.01 |
| Sodium citrate | 0.1 | 0.1 | 0.1 | 0.1 | 0.1 |
| Water | | | balance | | |
| Total | 100 | 100 | 100 | 100 | 100 |

BLENDING EXAMPLE 27

Shampooes having the formulations shown in Table 17 were prepared. They have no slimy feeling and good rinsing property.

TABLE 17

| Ingredient (%) | No. 1 | No. 2 | No. 3 | No. 4 |
|---|---|---|---|---|
| $C_8$ glucose ester | 10 | 10 | 10 | 10 |
| $C_{12}$, $C_{13}$ Sodium alkylsulfate | 5 | | | |
| $C_{10-18}$ α-olefin sulfonate | 5 | | | |
| Sodium N-methyl-N-oleoyl taurinate | | 10 | | |
| Sodium oleoylethyl succinate | | | 10 | |
| Polyoxyethylene lauryl ether ($\bar{p}$ = 7) | | | | 9 |
| Sodium polyoxyethylene lauryl ether sulfate ($\bar{p}$ = 3, alkyl group $C_{12}/C_{13}$ = 7/7) | 4 | 6 | 6 | |
| Paraffin sulfonate | 2 | | | 4 |
| Dimethyl polysiloxane (10,000 cs) | 2 | | 3 | 2 |
| Dimethyl polysiloxane (100,000 cs) | | 2 | | 1 |
| Yukafoamer AM75201 | 2 | 2 | | 2 |
| Yukafoamer AMW | | | 1 | 0.5 |
| Imidazolinium betaine (alkyl group: cocoyl) | | 5 | | 1 |
| Stearyl trimethyl ammonium chloride | | 1 | | 0.5 |
| Quaternary nitrogen-containing cellulose ether (nitrogen content: 2.0%, molecular weight: 100,000) | | 0.5 | 0.3 | 0.3 |
| Copolymer of dimethyldiallyl ammonium chloride and acrylamide (average molecular weight: 1,200,000) | | | 0.2 | |
| Coconut oil fatty acid diethanolamide | 4 | 2 | 2 | 2 |

TABLE 17-continued

| Ingredient (%) | No. 1 | No. 2 | No. 3 | No. 4 |
|---|---|---|---|---|
| Perfume | 0.4 | 0.4 | 0.4 | 0.4 |
| Dye (Yellow 203) | trace | trace | trace | trace |
| Citric acid | | (adjust pH to 5.8) | | |
| Purified water | | balance | | |
| Total | 100 | 100 | 100 | 100 |

BLENDING EXAMPLE 28

Shampooes having the formulations shown in Table 18 were prepared. They have no slimy feeling and good rinsing property.

TABLE 18

| Ingredient (%) | No. 1 | No. 2 | No. 3 | No. 4 | No. 5 |
|---|---|---|---|---|---|
| $C_{10}$ glucose ester | 15.0 | 15.0 | 15.0 | 15.0 | 15.0 |
| Sodium $C_{11}$, $C_{13}$ alkyl-sulfate | 3.0 | | | | |
| Sodium $C_{10-18}$ α-olefin sulfonate | | 3.0 | | | |
| N-lauroyl glutamate | | | 3.0 | | |
| Sodium octenyl succinate | | | | 5.0 | |
| Polyoxyethylene myristoyl ether (p = 5) | | | | | 5.0 |
| Polymer-JR-400 (manufactured by Union Carbide Co.) | 0.2 | 0.2 | 0.2 | 0.2 | 0.2 |
| Behenyl trimethyl ammonium chloride (average molecular weight: 404) | 2.42 | 2.42 | 2.42 | 2.42 | 2.42 |
| Sodium lauroyl alanine (average molecular weight: 307) | 1.23 | 1.23 | 1.23 | 1.23 | 1.23 |
| Propylene glycol | 5.0 | 5.0 | 5.0 | 5.0 | 5.0 |
| Polyoxyethylene (40 mol in average) hardened castor oil derivative | 2.0 | 2.0 | 2.0 | 2.0 | 2.0 |
| N-lauroyl dimethylamino acetic acid betaine | 5.0 | 5.0 | 5.0 | 5.0 | 5.0 |
| Dye, Perfume | appropriate amount | | | | |
| Ion-exchanged water | balance | | | | |
| Total | 100.0 | 100.0 | 100.0 | 100.0 | 100.0 |

BLENDING EXAMPLE 29

Body shampooes having the formulations shown in Table 19 were prepared. They have no slimy feeling and good rinsing property.

TABLE 19

| Ingredient (%) | No. 1 | No. 2 | No. 3 | No. 4 | No. 5 |
|---|---|---|---|---|---|
| $C_{10}$ glucose ester | 30.0 | 30.0 | 30.0 | 30.0 | 30.0 |
| Sodium $C_{12}$, $C_{13}$ alkyl-sulfate | 5.0 | | | | |
| Sodium $C_{10-18}$ α-olefin sulfonate | | 5.0 | | | |
| Sodium $C_{12}$ alaninate | | | 5.0 | | |
| Sodium $C_{15}$ alkyl succinate | | | | 5.0 | |
| Polyoxyethylene lauryl ether (p = 12) | | | | | 5.0 |
| Soap | | | | | 2.5 |
| Sodium lauroyl sarcosinate (average molecular weight: 310) | 0.93 | 0.93 | 0.93 | 0.93 | 0.93 |
| Lauryl imidazoline betaine | 10.0 | 10.0 | 10.0 | 10.0 | 10.0 |
| Dipropylene glycol | 8.0 | 8.0 | 8.0 | 8.0 | 8.0 |
| Aloe extract | 0.5 | 0.5 | 0.5 | 0.5 | 0.5 |
| Colorant, Perfume | appropriate amount | | | | |
| Preservative, Chelating agent | appropriate amount | | | | |
| Ion-exchanged water | balance | | | | |
| Total | 100.0 | 100.0 | 100.0 | 100.0 | 100.0 |

BLENDING EXAMPLE 30

Liquid detergents for cloth having the formulations shown in Table 20 were prepared. They have no slimy feeling and good rinsing property.

TABLE 20

| Ingredient (%) | No. 1 | No. 2 | No. 3 | No. 4 | No. 5 |
|---|---|---|---|---|---|
| $C_{10}$ glucose ester | 30.0 | 30.0 | 30.0 | 30.0 | 30.0 |
| Sodium $C_{12}$, $C_{13}$ alkyl-sulfate | 10.0 | | | | |
| Sodium $C_{10-18}$ α-olefin sulfonate | | 10.0 | | | |
| Sodium $C_{12}$ alaninate | | | 10.0 | | |
| Sodium $C_{15}$ alkyl succinate | | | | 10.0 | |
| Polyoxyethylene lauryl ether (p = 12) | | | | | 10.0 |
| Soap | | | | | 5.0 |
| Sodium xylene sulfonate | 5.0 | 5.0 | 5.0 | 5.0 | 5.0 |
| Sodium lauroyl alaninate (average molecular weight: 307) | 3.05 | 3.05 | 3.05 | 3.05 | 3.05 |
| Lauryl dimethylamino acetic acid betaine | 5.0 | 5.0 | 5.0 | 5.0 | 5.0 |
| Fluorescent dye | 0.2 | 0.2 | 0.2 | 0.2 | 0.2 |
| Ethanol | 8.0 | 8.0 | 8.0 | 8.0 | 8.0 |
| Dye, Perfume | appropriate amount | | | | |
| Sodium hydroxide | appropriate amount | | | | |
| Ion-exchanged water | balance | | | | |
| Total | 100.0 | 100.0 | 100.0 | 100.0 | 100.0 |

BLENDING EXAMPLE 31

Liquid dish-wash detergent having the following formulation was prepared. It has no slimy feeling and good rinsing property.

| | |
|---|---|
| $C_8$ glucose ester | 30% |
| Sodium $C_{12}$ higher alcohol polyoxyethylene sulfate (straight chain rate: 40%, p = 5) | 5 |
| Branched $C_{12}$ monoalkyl dimethylamine oxide (branching rate: 50%) | 8 |
| Keratin hydrolysis product (average molecular weight: 1000) | 0.1 |
| Sodium benzoate | 2 |
| Sodium p-toluene sulfonate | 4 |
| Ethanol | 7 |
| Alkanol amide | 2 |
| Perfume | 0.4 |
| Dye | 0.01 |

| | |
|---|---|
| Sodium citrate | 0.1 |
| Water | balance |
| Total | 100.0% |

BLENDING EXAMPLE 32

Shampooes having the formulations shown in Table 21 were prepared. They have was no slimy feeling and good rinsing property.

TABLE 21

| Ingredient (wt %) | No. 1 | No. 2 | No. 3 | No. 4 |
|---|---|---|---|---|
| $C_6$ glucose ester | 7 | | 1 | |
| $C_8$ glucose ester | | 6 | | |
| $C_{10}$ glucose ester | | | 8 | |
| $C_{12}$ arabinose ester | | | | 5 |
| Sodium polyoxyethylene lauryl ether sulfonate (p = 3, alkyl group $C_{12}/C_{13}$ = 1/1) | 7 | 5 | 5 | 9 |
| Paraffin sulfonate | 2 | | | 4 |
| Dimethyl polysiloxane (10,000 cs) | 2 | | 3 | 2 |
| Dimethyl polysiloxane (100,000 cs) | | 2 | | 1 |
| Yukafoamer AM75201 | 2 | 2 | | 2 |
| Yukafoamer AMW | | | 1 | 0.5 |
| Imidazolinium betaine (alkyl group:cocoyl) | | 5 | | 1 |
| Stearyl trimethyl ammonium chloride | | 1 | | 0.5 |
| Quaternary nitrogen-containing cellulose ether (nitrogen content: 2.0%, molecular weight: 100,000) | | 0.5 | 0.3 | 0.3 |
| Copolymer of dimethyldiallyl ammonium chloride and acrylamide (average molecular weight: 1,200,000) | | | 0.2 | |
| Coconut oil fatty acid diethanolamide | 4 | 2 | 2 | 2 |
| Perfume | 0.4 | 0.4 | 0.4 | 0.4 |
| Dye (Yellow 203) | trace | trace | trace | trace |
| Citric acid | | | (adjust pH to 5.8) | |
| Purified water | | | balance | |
| Total | 100.0 | 100.0 | 100.0 | 100.0 |

BLENDING EXAMPLE 33

Liquid dish-wash detergent having the following formulation was prepared. It has no slimy feeling and good rinsing property.

| | |
|---|---|
| $C_8$ glucose ester | 15.0% |
| Amine oxide | 3.0 |
| Polymer-JR-400 (manufactured by by Union Carbide Co.) | 0.2 |
| Behenyl trimethyl ammonium chloride (Average molecular weight: 404) | 2.42 |
| Propylene glycol | 5.0 |
| Polyoxyethylene (average 40 mol) hardened castor oil | 2.0 |
| N-lauryl dimethylamino acetic acid betaine | 5.0 |
| Dye, Perfume | appropriate amount |
| Ion-exchanged water | balance |
| Total | 100.0% |

BLENDING EXAMPLE 34

Body shampoo having the following formulation was prepared. It has no slimy feeling and good rinsing property.

| | |
|---|---|
| $C_{10}$ glucose ester | 30.0% |
| $C_{14}$ monoalkyl dimethyl amine oxide | 2.0 |
| Sodium coconut oil fatty acid methyl-$\beta$-alaninate | 3.0 |
| Lauroyl imidazoline betaine | 10.0 |
| Dipropylene glycol | 8.0 |
| Aloe extract | 0.5 |
| Dye, Perfume | appropriate amount |
| Preservative and Chelating agent | appropriate amount |
| Ion-exchanged water | balance |
| Total | 100.0% |

BLENDING EXAMPLE 35

Liquid detergent for cloth having the following formulation was prepared. It has no slimy feeling and good rinsing property.

| | |
|---|---|
| $C_{12}$ glucose ester | 30.0% |
| Amine oxide | 5.0 |
| $C_{12}$ alkyl ether (p = 7) | 5.0 |
| Lauryl dimethyl amino acetic acid betaine | 5.0 |
| Fluorescent dye | 0.2 |
| Ethanol | 8.0 |
| Dye, Perfume | appropriate amount |
| Sodium hydroxide | appropriate amount |
| Ion-exchanged water | balance |
| Total | 100.0% |

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A nonionic surface active agent comprising a fatty acid ester of a hexose or an alkyl glycoside thereof, wherein the content of monoester is from 93 to 99.9% by weight, the content of diester is from 0.1 to 7% by weight and the content of tri- and higher polyesters is from 0 to 1% by weight in said fatty acid ester.

2. The nonionic surface active agent as defined in claim 1, wherein the hexose is glucose.

3. The nonionic surface active agent as defined in claim 1, wherein the alkyl group of the alkyl glycoside has 1 to 6 carbon atoms.

4. The nonionic surface active agent as defined in claim 1, wherein the fatty acid has 6 to 20 carbon atoms.

5. The nonionic surface active agent as defined in claim 1, wherein said monoester is represented by the following formula (I):

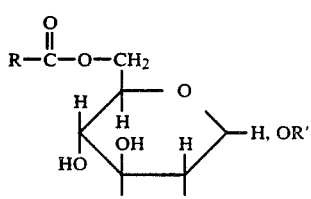

where R represents a fatty acid radical having 6 to 20 and R' represents a hydrogen atom or an alkyl group having 1 to 6 carbon atoms.

6. The nonionic surface active agent as defined in claim 1, wherein the content of said monoester is from 96 to 99.8% by weight, the content of said diester is from 0.2 to 4% by weight, and the content of said tri- and higher polyesters is from 0 to 0.5% by weight in said fatty acid ester.

7. A nonionic surface active agent comprising a fatty acid ester of glucose or an alkyl glycoside thereof, wherein the content of monoester is from 96 to 99.8% by weight, the content of diester is from 0.2 to 4% by weight and the content of tri- and higher polyesters if from 0 to 0.5% by weight in said fatty acid ester.

* * * * *

UNITED STATES PATENT AND TRADEMARK OFFICE
CERTIFICATE OF CORRECTION

PATENT NO. : 5,109,127
DATED : April 28, 1992
INVENTOR(S) : Sekiguchi, et al

It is certified that error appears in the above-identified patent and that said Letters Patent is hereby corrected as shown below:

Col. 32, line 45, change "01" to --0.1--.

Signed and Sealed this

Tenth Day of August, 1993

Attest:

MICHAEL K. KIRK

Attesting Officer

Acting Commissioner of Patents and Trademarks